United States Patent

Claussner et al.

[11] Patent Number: 6,087,509
[45] Date of Patent: Jul. 11, 2000

[54] 1-IMIDAZOLIDINYL-PHENYLS

[75] Inventors: Andre Claussner, Villemomble; Francois Goubet, Paris; Jean-George Teutsch, Pantin, all of France

[73] Assignee: Hoechst Marion Roussel, France

[21] Appl. No.: 09/077,223

[22] PCT Filed: Nov. 21, 1996

[86] PCT No.: PCT/FR96/01846

§ 371 Date: Jun. 23, 1998

§ 102(e) Date: Jun. 23, 1998

[87] PCT Pub. No.: WO97/19064

PCT Pub. Date: May 29, 1997

[30] Foreign Application Priority Data

Nov. 22, 1995 [FR] France .................................. 9513836

[51] Int. Cl.[7] .................... C07D 233/76; C07D 233/72; C07D 233/78; C07D 235/02; C07D 405/12; A61K 31/4166; A61N 5/28; A61N 17/10

[52] U.S. Cl. .................... 548/307.1; 514/396; 514/397; 514/398; 514/399; 514/400; 548/219.1; 548/320; 548/320.5; 548/321.1

[58] Field of Search ............... 548/320.1, 321.1, 548/320.5, 317.1, 300.7; 514/398, 399, 396, 397

[56] References Cited

U.S. PATENT DOCUMENTS

| | | | |
|---|---|---|---|
| 4,407,814 | 10/1983 | Bernauber et al. | 548/321.1 X |
| 4,473,393 | 9/1984 | Nagpal | 548/320.1 X |
| 4,944,791 | 7/1990 | Schroder et al. | 548/321.1 X |
| 4,958,028 | 9/1990 | Prisbylla | 548/321.1 |
| 5,166,358 | 11/1992 | Seuron et al. | 548/321.1 |
| 5,411,981 | 5/1995 | Gaillard-Kelly et al. | 514/386 |
| 5,434,176 | 7/1995 | Claussner et al. | 514/391 |
| 5,656,651 | 8/1997 | Sovak et al. | 514/396 |

FOREIGN PATENT DOCUMENTS

| | | |
|---|---|---|
| 494819 | 7/1992 | European Pat. Off. . |
| 578516 | 1/1994 | European Pat. Off. . |
| 0704448 | 4/1996 | European Pat. Off. . |
| 2693461 | 1/1994 | France . |
| 52-000270 | 1/1977 | Japan .................. 548/320.1 |
| 95187947 | 7/1995 | WIPO . |

*Primary Examiner*—Floyd D. Higel
*Attorney, Agent, or Firm*—Bierman, Muserlian and Lucas

[57] ABSTRACT

A particular subject of the invention is the products of formula (I):

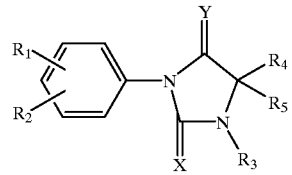

in which:

$R_1$ and $R_2$ represent in particular cyano and trifluoromethyl, $R_3$ represents in particular alkyl, alkenyl or alkynyl, optionally substituted by one or more halogen, cyano or hydroxyl radicals, $R_4$ and $R_5$ either represent in particular methyl optionally substituted by fluorine, or form in particular a cyclohexyl radical, X and Y represent in particular oxygen, as well as their salts and isomers.

3 Claims, No Drawings

1-IMIDAZOLIDINYL-PHENYLS

This application is a 371 PCT/FR96/01846 filed Nov. 21, 1996.

The present invention relates to new fluorinated or hydroxylated phenylimidazolidines, their preparation process, the new intermediates obtained, their use as medicaments, their new use and the pharmaceutical compositions containing them.

A subject of the present invention is the products of formula (I):

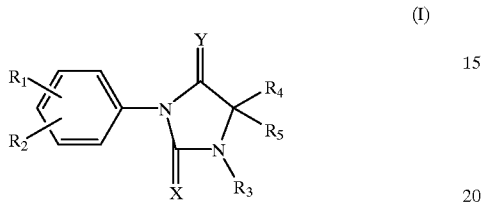

in which:
- $R_1$ and $R_2$, identical or different, are chosen from cyano, nitro, trifluoromethyl radicals and halogen atoms,
- $R_3$ represents a linear or branched aryl, arylalkyl, alkyl, alkenyl or alkynyl radical containing at most 10 carbon atoms and optionally substituted by one or more radicals chosen from halogen atoms and cyano, hydroxyl, alkoxy, carboxy, acyl and acyloxy radicals, in which, if appropriate, the alkyl, alkoxy and acyl radicals are linear or branched, containing at most 10 carbon atoms, the carboxy radical is free, salified, esterified or amidified and the hydroxy radical is free, esterified, etherified or protected,
- $R_4$ and $R_5$ identical or different, represent a linear or branched alkyl radical containing at most 4 carbon atoms and optionally substituted by a halogen atom, or form with the carbon atom to which they are linked a cyclic radical constituted by 3 to 7 members and optionally containing one or more identical or different heteroatoms, chosen from oxygen, sulphur or nitrogen atoms,
- X and Y, identical or different, represent an oxygen or sulphur atom, said products of formula (I) being in all the possible racemic, enantiomeric and diastereoisomeric isomer forms, as well as the addition salts with mineral and organic acids or with mineral and organic bases of said products of formula (I).

In the products of formula (I) and in what follows:
the term halogen designates fluorine, chlorine, bromine or iodine atoms, The fluorine, chlorine or bromine atoms are preferred.

The term linear or branched alkyl radical designates the following radicals: methyl, ethyl, propyl, isopropyl, butyl, isobutyl, sec-butyl, tert-butyl, pentyl, isopentyl, hexyl, isohexyl and also heptyl, octyl, nonyl and decyl, as well as their linear or branched position isomers, Alkyl radicals having at most 6 carbon atoms are preferred and in particular the methyl, ethyl, propyl, isopropyl, n-butyl, n-pentyl and n-hexyl radicals.

The term linear or branched alkenyl radical designates the vinyl, allyl, 1-propenyl, butenyl, 1-butenyl, pentenyl or hexenyl radicals as well as their linear or branched position isomers.

Among the alkenyl radicals, the vinyl, allyl, n-butenyl or isobutenyl values are preferred.

The term alkynyl designates a linear or branched radical having at most 12 carbon atoms such as for example ethynyl, propargyl, butynyl, pentynyl or hexynyl.

Among the alkynyl radicals, those with 4 carbon atoms are preferred and in particular the propargyl radical.

The term linear or branched alkoxy radical designates the methoxy, ethoxy, propoxy, isopropoxy, Linear, secondary or tertiary butoxy, pentoxy or hexoxy radicals as well as their linear or branched position isomers.

The term cyclic radical constituted by 3 to 7 members and optionally containing one or more identical or different heteroatoms, chosen from oxygen, sulphur or nitrogen atoms, designates on the one hand a cycloalkyl radical which itself designates in particular the cyclobutyl, cyclopentyl and cyclohexyl radicals and on the other hand a carbocyclic radical interrupted by one or more heteroatoms chosen from oxygen, nitrogen or sulphur atoms such as quite particularly the saturated monocyclic heterocyclic radicals such as for example the following radicals: oxetannyl, oxolannyl, dioxanyl, dithiolane, thiooxolane, thiooxane, pyrrolidinyl, piperidyl, piperazinyl, morpholinyl, azetidine, oxetane and thietane.

The term acyl radical preferably designates the formyl, acetyl, propionyl, butyryl and benzoyl radicals, but also the valeryl, hexanoyl, acryloyl, crotonoyl and carbamoyl radicals.

The term acyloxy radical designates the radicals in which the acyl radicals have the meaning indicated above and for example the acetoxy or propionyloxy radicals.

The term aryl designates the carbocyclic aryl radicals such as phenyl or naphthyl and the heterocyclic monocyclic aryl radicals with 5 or 6 members or constituted by condensed rings, containing one or more heteroatoms preferably chosen from oxygen, sulphur and nitrogen. Among the heterocyclic aryl radicals with 5 members the following radicals can be mentioned: furyl, thienyl, pyrrolyl, thiazolyl, oxazolyl, imidazolyl, thiadiazolyl, pyrazolyl, isoxazolyl, tetrazolyl.

Among the heterocyclic aryl radicals with 6 members, the pyridyl, pyrimidinyl, pyridazinyl, pyrazinyl radicals can be mentioned.

Among the condensed aryl radicals, the indolyl, benzofuranyl, benzothienyl, quinolinyl radicals can be mentioned.

The phenyl, tetrazolyl and pyridyl radicals are preferred.

The term arylalkyl designates the radicals resulting from the combination of the alkyl radicals and the aryl radicals mentioned above.

The benzyl, phenylethyl, pyridylmethyl, pyridylethyl or tetrazolylmethyl radicals are preferred.

As particular examples of alkyl radicals substituted by one or more halogens, the monofluoro-, chloro- or bromomethyl, difluoro-, dichloro- or dibromo-methyl and trifluoromethyl radicals can be mentioned.

The carboxy radical or radicals of the products of formula (I) can be free, salified, esterified or amidified by the various groups known to a man skilled in the art.

There can be mentioned, for example:
the carboxy radicals salified by mineral bases such as, for example, an equivalent of sodium, potassium, lithium, calcium, magnesium or ammonium or organic bases such as, for example, methylamine, propylamine, trimethylamine, diethylamine, triethylamine, N,N- dimethylethanolamine, tris (hydroxymethyl) amino methane, ethanolamine, pyridine, picoline, dicyclohexylamine, morpholine, benzylamine, procaine, lysine, arginine, histidine, N-methylglucamine.

The sodium or potassium salts are preferred.

the carboxy radicals esterified by alkyl radicals in order to form alkoxy carbonyl groups such as, for example, methoxycarbonyl, ethoxycarbonyl, propoxycarbonyl, butoxy-, isobutoxy- and tert-butoxy-carbonyl or benzyloxycarbonyl, these alkyl radicals being able to be substituted by radicals chosen for example from halogen atoms, hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

The radicals formed with the easily cleavable ester remainders can also be mentioned, such as the methoxymethyl, ethoxymethyl radicals; the acyloxyalkyl radicals such as pivaloyloxymethyl, pivaloyloxyethyl, acetoxymethyl or acetoxyethyl; the alkyloxycarbonyloxy alkyl radicals such as the methoxycarbonyloxy methyl or ethyl radicals, the isopropyloxycarbonyloxy methyl or ethyl radicals.

A list of such ester radicals can be found for example in the European Patent EP 0,034,536.

By amidified carboxy is meant the groups of —CON(R$_6$) (R$_7$) type in which the R$_6$ and R$_7$ radical identical or different represent a hydrogen atom or an alkyl radical having 1 to 4 carbon atoms such as the following radicals: methyl, ethyl, propyl, isopropyl, butyl, isobutyl, sec-butyl or tert-butyl.

Among the —CON(R$_6$)(R$_7$) groups defined above, those in which the —N(R$_6$)(R$_7$) represents the amino, mono- or dimethylamino radical are preferred.

The N(R$_6$)(R$_7$) radical can also represent a heterocycle which may or may not contain an additional heteroatom. The pyrrolyl, imidazolyl, indolyl, piperidino, morpholino, piperazinyl radicals can be mentioned. The piperidino or morpholino radicals are preferred.

By esterified, etherified or protected hydroxyl radical is meant the

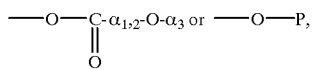

radicals respectively, formed from an —OH hydroxyl radical, according to the usual methods known to a man skilled in the art and in which P represents a protective group, α$_1$, α$_2$ and α$_3$ represent in particular an alkyl, alkenyl, alkynyl, aryl or arylalkyl radical, having at most 12 carbon atoms and optionally substituted as is defined above in particular for R$_3$.

Examples of the protective group P, as well as the formation of the protected hydroxyl radical, are given in particular in the usual book of a man skilled in the art: Protective Groups in Organic Synthesis, Theodora W. Greene, Harvard University, printed in 1981 by Wiley-Interscience Publishers, John Wiley & Sons.

The protective group of the hydroxyl radical which can be represented by P, can be chosen from the list below: for example formyl, acetyl, chloroacetyl, bromoacetyl, dichloroacetyl, trichloroacetyl, trifluoroacetyl, methoxyacetyl, phenoxyacetyl, benzoyl, benzoylformyl, p-nitrobenzoyl. The following groups can also be mentioned: ethoxycarbonyl, methoxycarbonyl, propoxycarbonyl, βββ-trichloroethoxy-carbonyl, benzyloxycarbonyl, tertbutoxycarbonyl, 1-cyclo propylethoxycarbonyl, tetrahydropyrannyl, tetrahydrothiopyrannyl, methoxytetrahydropyrannyl, trityl, benzyl, 4-methoxybenzyl, benzhydryl, trichloroethyl, 1-methyl 1-methoxyethyl, phthaloyl, propionyl, butyryl, isobutyryl, valeryl, isovaleryl, oxalyl, succinyl and pivaloyl, phenylacetyl, phenylpropionyl, mesyl, chlorobenzoyl, para-nitrobenzoyl, para-tert-butylbenzoyl, caprylyl, acryloyl, methylcarbamoyl, phenylcarbamoyl, naphthylcarbamoyl.

P can in particular represent the radical

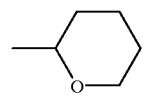

or also a silicon derivative such as trimethylsilyl.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic such as for example methanesulphonic, ethanesulphonic, propanesulphonic, alkyldisulphonic such as for example methanedisulphonic, alpha, beta-ethanedisulphonic, arylmonosulphonic such as benzenesulphonic and aryldisulphonic.

There can be mentioned more particularly the salts formed with the hydrochloric or methanesulphonic acids for example.

It can be remembered that stereoisomerism can be defined as the isomerism of compounds having the same developed formulae, but the various groups of which are arranged differently in space, such as in particular in the boat and chair shapes of cyclohexane and mono-substituted cyclohexanes whose substituent can be in axial or equatorial position, and the various possible rotational conformations of ethane derivatives. However, another type of stereoisomerism exists, due to the different spatial arrangements of fixed substituents, either on double bonds, or on rings, which is often called geometrical isomerism or cis-trans isomerism. The term stereoisomeric is used in the present Application in its broadest sense and therefore relates to all of the compounds indicated above.

In the products of formula (I) and in what follows, it can be noted that:

the hydrogen atoms which are contained by the optionally substituted alkyl or alkenyl radicals which can be represented by R$_3$ can be deuterium atoms, the fluorine atoms which can be represented by halogen atoms can be an $^{18}$F atom which is useful for medical imagery.

Thus a subject of the present invention is the products of formula (I) as defined above, in which: R$_1$ and R$_2$ both represent a chlorine atom, or being identical or different are chosen from the cyano, nitro and trifluoromethyl radical, R$_3$ represents a linear or branched phenyl, pyridyl, phenylalkyl, pyridylalkyl, alkyl, alkenyl or alkynyl radical containing at most 4 carbon atoms and optionally substituted by one or more radicals chosen from halogen atoms and cyano, hydroxyl, alkoxy, acyl and acyloxy radicals, in which if appropriate, the acyl and alkoxy radicals are linear or branched, containing at most 6 carbon atoms and the hydroxyl radical is free, esterified or protected, $R_4$ and $R_5$, identical or different, represent a methyl radical optionally substituted by a halogen atom, or form with the carbon atom to which they are linked a cyclobutyl, cyclopentyl, cyclohexyl, dioxane radical, or a

radical in which W represents an oxygen or sulphur atom or the —NH radical,

X and Y, identical or different, represent an oxygen or sulphur atom, said products of formula (I) being in all the possible racemic, enantiomeric and diastereoisomeric isomer forms, as well as the addition salts with mineral and organic acids or with mineral and organic bases of said products of formula (I).

The

radical represents in particular the piperidyl or tetrahydropyran radical.

A particular subject of the present invention is the products of formula (I) as defined above, in which:

$R_1$ and $R_2$ represent a cyano radical and a trifluoromethyl radical, $R_3$ represents a linear or branched alkyl, alkenyl or alkynyl radical, containing at most 4 carbon atoms and optionally substituted by one or more radicals chosen from halogen atoms, the cyano radical and the free, esterified or protected hydroxyl radical, $R_4$ and $R_5$, identical or different, represent a methyl radical optionally substituted by a fluorine atom, or form with the carbon atom to which they are attached a cyclohexyl radical X and Y represent an oxygen atom, said products of formula (I) being in all the possible racemic, enantiomeric and diastereoisomeric isomer forms, as well as the addition salts with mineral and organic acids or with mineral and organic bases of said products of formula (I).

Among the preferred products of the invention, there can be mentioned more particularly the products of formula (I) as defined above the names of which follow:

4-(4,4-bis(fluoromethyl)-2,5-dioxo-3-(2-fluoroethyl)-1-imidazolidinyl)-2-(trifluoromethyl)-benzonitrile, 4-(2,5-dioxo-4,4-bis(fluoromethyl)-3-ethyl-1-imidazolidinyl)-2-(trifluoromethyl)-benzonitrile, 4-(4,4-bis(fluoromethyl)-2,5-dioxo-3-(4-hydroxy-2-butyn-1-yl)-1-imidazolidinyl)-2-(trifluoromethyl)-benzonitrile, 4-(3-(4-hydroxy-2-butyn-1-yl)-4,4-dimethyl-2,5-dione-1-imidazolidinyl)-2-(trifluoromethyl)-benzonitrile, 4-[2,4-dioxo-1-(4-hydroxybutyl)-1,3-diazaspiro[4.5]decan-3-yl]-2-(trifluoromethyl)-benzonitrile, said products of formula (I) being in all the possible racemic, enantiomeric and diastereoisomeric isomer forms, as well as the addition salts with mineral and organic acids or with mineral and organic bases of said products of formula (I).

Also a subject of the present invention is a preparation process for the products of formula (I), as defined above, characterized in that, in the presence of a tertiary base, a product of formula (II):

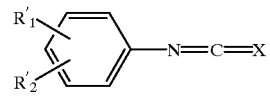

(II)

in which $R'_1$ and $R'_2$ have the meanings indicated above, for $R_1$ and $R_2$ respectively, in which the optional reactive functions are optionally protected and X has the meaning indicated above, is reacted with a product of formula (III):

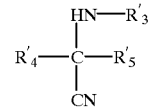

(III)

in which $R'_3$, $R'_4$ and $R'_5$ have the meanings indicated above, for $R_3$, $R_4$ and $R_5$ respectively in which the optional reactive functions are optionally protected, in order to obtain a product of formula (IV):

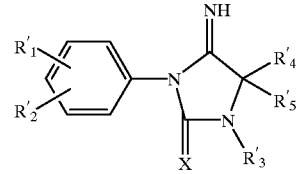

(IV)

in which X, $R'_1$, $R'_2$, $R'_3$, $R'_4$ and $R'_5$ have the meanings indicated above, which is converted into a product of formula (V):

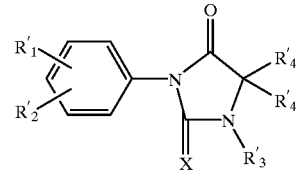

(V)

in which X, $R'_1$, $R'_2$, $R'_3$, $R'_4$ and $R'_5$ have the meanings indicated above, which products of formulae (IV) and (V), if necessary or if desired, in order to obtain products of formula (I) as defined above, can be subjected to any one or more of the following reactions, in any order:

a) if appropriate conversion of the >C=S group which can be represented by >C=X in the >C=O group, b) the action on the products of formula (V) in which $R'_3$ represents a hydrogen atom, of a reagent of formula Hal–$R''_3$ in which $R''_3$ has the values indicated above for $R_3$, with the exception of the hydrogen value, and in which the optional reactive functions are optionally protected, and Hal represents a halogen atom, in order to obtain the corresponding products, in which R'$_3$ is replaced by R"$_3$, c) release of the OH radical which can be carried by one or both of R'$_4$ and R'$_5$ and/or R'$_3$, d) esterification or conversion of the OH radical into a halogen radical, e) elimination reaction of the optional protective groups, f) if appropriate the action of an esterification, amidification or salification agent, g) resolution reaction of the racemic forms, said products of formula (I) thus obtained being in all the possible racemic, enantiomeric and diastereoisomeric isomer forms.

The action of the products of formula (II) with the products of formula (III) in order to obtain the products of formula (IV) can be carried out in an organic solvent such as tetrahydrofuran or dichloroethane but ethyl ether or isopropyl ether can also be used.

The operation is carried out in the presence of a tertiary base such as triethylamine or also pyridine or methylethylpyridine.

The optional reactive functions which are optionally protected can be in particular the hydroxy or amino functions. The usual protective groups are used to protect these functions. The following protective groups of the amino radical can for example be mentioned: tert-butyl, tertamyl, trichloroacetyl, chloroacetyl, benzhydryl, trityl, formyl, benzyloxycarbonyl, terbutyloxycarbonyl.

As the protective group of the hydroxy radical there can be mentioned for example the tetrahydropyrannyl, trimethylsilyl, triphenylmethyl or tert-butyl dimethylsilyl radicals.

Of course the above list is not limitative and other protective groups, for example known in the chemistry of the peptides, can be used. A list of such protective groups is found for example in the French Patent BF 2,499,995 whose content is incorporated here by reference.

In the product of formula (III), R$_4$ and R$_5$ can form a cyclic radical with the carbon atom that carries them, such as in particular a cyclohexyl radical.

Also, in the product of formula (III), one or both of R$_4$ and R$_5$ may or may not carry a hydroxyl radical which can be protected in particular as an -O-tetrahydropyrannyl (OTHP).

The reaction of the product of formula (II) as defined above with a product of formula (III) as defined above in order to produce the corresponding product of formula (IV), can then be carried out in particular in the presence of methylene chloride at a temperature of about –30° C.

The optional elimination reactions of the protective groups are carried out according to the usual methods known to a man skilled in the art or, for example, as indicated in the Patent BF 2,499,995. The preferred method of elimination is acid hydrolysis using acids chosen from hydrochloric, benzene sulphonic or paratoluene sulphonic, formic or trifluoroacetic acids. Hydrochloric acid is preferred.

The optional hydrolysis reaction of the >C=NH group into the carbonyl group in order to convert in particular the product of formula (IV) into the product of formula (V) is preferably carried out using an acid such as aqueous hydrochloric acid, for example under reflux.

The action on the products of formula (V) of the reagent of formula Hal–R"$_3$ is carried out in the presence of a strong base such as sodium or potassium hydride. The operation can be carried out by phase transfer reaction in the presence of quaternary ammonium salts such as tetrabutyl ammonium dihydrogen phosphate salts.

The conversion of the OH radical into the halogen radical can be carried out under the usual conditions known to a man skilled in the art such as in particular in a solvent such as for example tetrahydrofuran and by the action of a halogenated derivative such as in particular, when the halogen atom is a fluorine atom, diethylaminosulphide trifluoride (DAST).

Triflic anhydride can also be reacted beforehand in order to obtain the corresponding triflate which is then exchanged with the corresponding fluoride as described hereafter in the examples and in particular by the action of tetrabutylammonium fluoride.

When the halogen atom is a bromine, chlorine or iodine atom, the action can be carried out according to the usual conditions known to a man skilled in the art such as in particular by the action, in the presence of triphenylphosphine, of the corresponding halogenating agent such as for example carbon tetrabromide, carbon tetrachloride or also iodine.

The optional esterification of the products of formula (IV), (V) or (I) as defined above, which contain one or more free OH radicals is carried out under standard conditions. For example an acid or a functional derivative can be used, for example an anhydride such as acetic anhydride in the presence of a base such as pyridine.

The optional esterification or salification of the products of formula (IV), (V) or (I) as defined above, which contain one or more COOH groups, is carried out under standard conditions known to a man skilled in the art.

The optional amidification of the products of formula (IV), (V) or (I) as defined above, which contain a COOH radical, is carried out under standard conditions. A primary or secondary amine can be used on a functional derivative of the acid, for example a symmetrical or mixed anhydride.

Also a subject of the present invention is a preparation process for the products of formula (I'):

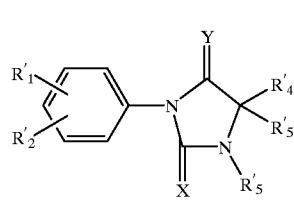

(I')

in which X, Y, R'$_1$, R'$_2$, R'$_3$, R'$_4$ and R'$_5$ are as defined above, process characterized in that a product of formula

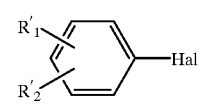

(VII)

in which R'$_1$ and R'$_2$ have the previous meanings and Hal represents a halogen atom, is reacted with a product of formula (VI):

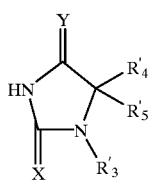

(VI)

in which X, Y, R'₃, R'₄ and R'₅ have the meanings indicated above, the reaction being carried out in the presence of a catalyst and optionally of a solvent.

With regard to the products of formula (VI), the term Hal preferably designates the chlorine atom, but can also represent a bromine or iodine atom.

The reaction conditions of such a process are in particular those described in EP 0,494,819.

The products which are a subject of the present invention possess useful pharmacological properties, in particular they fix themselves on the androgen receptor and they have an anti-androgenic activity.

Tests given in the experimental part illustrate these properties.

These properties make the products of formula (I) as defined above of the present invention of use as medicaments mainly for:

the treatment of adenomas and neoplasias of the prostate as well as benign hypertrophy of the prostate, on its own or combined with analogues of LHRH. They can also be used in the treatment of benign or malignant tumours possessing androgen receptors and more particularly cancers of the breast, the skin, the ovaries, the bladder, the lymphatic system, the kidneys and the liver, the treatment of cutaneous affections such as acne, hyperseborrhea, alopecia or hirsutism. These products can therefore be used in dermatology on their own or combined with antibiotics such as derivatives of azelaic and fusidic acids, erythromycin, as well as derivatives of retinoic acid or an inhibitor of 5alpha-reductase such as (5alpha,17beta)-1,1-dimethylethyl 3-oxo 4-aza-androst-1-ene 17-carboxamide (or Finasteride, Merck 11th Ed.) for the treatment of acne, alopecia or hirsutism. They can also be combined with a product stimulating hair growth such as Minoxidil for the treatment of alopecia.

The products of formula (I), as defined above, in radio-active form (tritium, carbon 14, iodine 125 or fluorine 18) can also be used as specific labels for the androgen receptors. They can also be used in diagnostics for medical imagery.

The products of formula (I) as defined above can also be used in the veterinary domain for the treatment of behavioural disorders such as aggressiveness, androgen-dependent affections, such as circum analum in dogs and tumours having androgen receptors. They can also be used to bring about a chemical castration in animals.

Therefore a subject of the invention is the use, as medicaments, of the products of formula (I) as defined above, said products of formula (I) being in all the possible racemic or optically-active isomer forms, as well as the addition salts with pharmaceutically acceptable mineral or organic acids or mineral and organic bases of said products of formula (I).

A particular subject of the invention is the use, as medicaments of the products of formula (I) as defined above, in which:

$R_1$ and $R_2$ represent a cyano radical and a trifluoromethyl radical, $R_3$ represents a linear or branched alkyl, alkenyl or alkynyl radical, containing at most 4 carbon atoms and optionally substituted by one or more radicals chosen from halogen atoms, the cyano radical and the free, salified or protected hydroxyl radical, $R_4$ and $R_5$ are either identical or different and represent a methyl radical optionally substituted by a fluorine atom, or form with the carbon atom to which they are attached a cyclohexyl radical, X and Y represent an oxygen atom, said products of formula (I) being in all the possible racemic, enantiomeric and diastereoisomeric isomer forms, as well as the addition salts with pharmaceutically acceptable mineral and organic acids or mineral and organic bases of said products of formula (I).

Also a subject of the invention is the use, as medicaments, of the following products:

4-(4,4-bis(fluoromethyl)-2,5-dioxo-3-(2-fluoroethyl)-1-imidazolidinyl)-2-(trifluoromethyl)-benzonitrile, 4-(2,5-dioxo-4,4-bis(fluoromethyl)-3-ethyl-1-imidazolidinyl)-2-(trifluoromethyl)-benzonitrile, 4-(4,4-bis(fluoromethyl)-2,5-dioxo-3-(4-hydroxy-2-butyn-1-yl)-1-imidazolidinyl)-2-(trifluoromethyl)-benzonitrile, 4-(3-(4-hydroxy-2-butyn-1-yl)-4,4-dimethyl-2,5-dioxo-1-imidazolidinyl)-2-(trifluoromethyl)-benzonitrile, 4-[2,4-dioxo-1-(4-hydroxybutyl)-1,3-diazaspiro[4.5]decan-3-yl]-2-(trifluoromethyl)-benzonitrile, said products of formula (I) being in all the possible racemic, enantiomeric and diastereoisomeric isomer forms, as well as the addition salts with pharmaceutically acceptable mineral and organic acids or mineral and organic bases of said products of formula (I).

The products can be administered by parenteral, buccal, perlingual, rectal or topical route.

Also a subject of the invention is the pharmaceutical compositions, characterized in that they contain, as active ingredient, at least one of the medicaments of formula (I), as defined above.

These compositions can be presented in the form of injectable solutions or suspensions, tablets, coated tablets, capsules, syrups, suppositories, creams, ointments and lotions. These pharmaceutical forms are prepared according to the usual methods. The active ingredient can be incorporated with excipients usually employed in these compositions, such as aqueous or non-aqueous vehicles, talc, gum arabic, lactose, starch, magnesium stearate, cocoa butter, fatty substances of animal or vegetable origin, paraffin derivatives, glycols, various wetting, dispersing or emulsifying agents, preservatives.

The usual dose, variable according to the patient treated and the affection in question, can be, for example, from 10 mg to 500 mg per day in man, by oral route.

The products of formula (II) used at the start of the invention can be obtained by the action of phosgene when X represents an oxygen atom or thiophosgene when X represents a sulphur atom on the corresponding amine of formula (A):

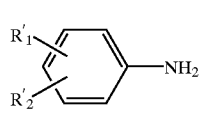

in which R'$_1$ and R'$_2$ have the meanings indicated above.

A product of this type is in particular described in the French Patent BF 2,329,276.

Amines of formula (A) are described in the European Patent EP 0,002,892 or the French Patent BF 2,142,804. The products of formula (III) are known or can be prepared from the corresponding cyanohydrin according to the process described in the publications: J. Am. Chem. Soc. (1953), 75, 4841, BEIL I 4 526 or J. Org. Chem. 27 2901 (1962).

The products of formula (III) in which R'$_3$ is different from a hydrogen atom can be obtained by the action of a product of formula R"$_3$ Hal on 2-cyano 2-amino propane under the conditions stated above for the action of R"$_3$ Hal on the products of formula (V). An example of this type of preparation is described in the reference:

Jilek et al. Collect. Czech. Chem. Comm. 54(8) 2248 (1989).

The products of formulae (VII) and (VI), used at the start of the process indicated above, for obtaining products of formula (I), as defined above, are known and commercially available or can be prepared according to methods known to a man skilled in the art.

The preparation of products of formula (VI) is described in particular in the following publications:

Zhur. Préklad. Khim. 28, 969–75 (1955) (CA 50, 4881a, 1956)

Tetrahedron 43, 1753 (1987)

J. Org. Chem. 52, 2407 (1987)

Zh. Org. Khim. 21, 2006 (1985)

J. Fluor. Chem. 17, 345 (1981) or in the:

German Patent DRP 637,318 (1935)

European Patent EP 0,130,875

Japanese Patent JP 81,121,524.

The products of formula (VI) which are hydantoin derivatives are widely used and mentioned in the literature such as for example in the following articles:

J. Pharm. Pharmacol., 67, Vol. 19(4), p. 209–16 (1967)

Khim. Farm. Zh., 67, Vol. 1 (5) p. 51–2

German Patent 2,217,914

European Patent 0,091,596

J. Chem. Soc. Perkin. Trans. 1, p. 219–21 (1974).

Also a subject of the invention is, as new industrial products and in particular as new industrial products which can be used as intermediate products for the preparation of the products of formula (I) as defined above, the products of formulae (IV) and (V) as defined above and notably the products of formula (V) in which R$_4$ and R$_5$ represent an alkyl radical substituted by a free, esterified, etherified or protected hydroxyl radical.

Also a subject of the present invention is the use of the products of formula (I) as defined above, for the preparation of pharmaceutical compositions intended for the treatment of adenomas and neoplasias of the prostate as well as of benign hypertrophy of the prostate, on their own or combined with analogues of LHRH, for the treatment of cutaneous affections such as acne, hyperseborrhea, alopecia or hirsutism or in diagnostics for medical imagery.

The following examples illustrate the invention without however limiting it.

Preparation 1

2-(trifluoromethyl) benzonitrile 4-isocyanate.

10 g of 4-cyano 3-(trifluoromethyl) aniline (described in the European Patent EP 0,002,892) in solution in 30 ml of ethyl acetate is added over 20 minutes to 33.6 ml of a toluenic solution of phosgene at 1.93 M/l cooled down to 0/5° C. Agitation is carried out for 30 minutes at this temperature then the reaction medium is left to rise to 25° C. It is heated until distillation is achieved, compensating for the volume distilled off with toluene until the distillation temperature reaches 110° C. Reflux is maintained until the release of hydrochloric acid has stopped (i.e. 4 hours 30 minutes). The medium is returned to ambient temperature, the insoluble part is separated out over sodium sulphate under an inert atmosphere, followed by rinsing three times with 10 ml of toluene and evaporating to dryness under reduced pressure. After heating at 60° C. for one hour, the temperature is returned to ambient under inert atmosphere and 11.6 g of expected product is obtained.

ANALYSES:

| Infra-red (cm$^{-1}$) | |
|---|---|
| —N=C=O | 2268 |
| —CN | 2233 |

EXAMPLE 1

4-(4,4-bis(fluoromethyl)-2,5-dioxo-3-(2-fluoroethyl)-1-imidazolidinyl)-2-(trifluoromethyl)-benzonitrile STAGE 1: 1,3 bis [(tetrahydro-2H-pyran-2-yl)oxy]-2-propanone 9 g of 2,5-dihydroxy-1,4-dioxane-2,5-dimethanol is introduced into 60 ml of dioxane and the suspension is taken to about 70° C. for 15 minutes then returned to ambient temperature. 20 ml of 3,4-dihydro 2H-pyran and 300 mg of monohydrated paratoluene sulphonic acid are then added and the temperature is maintained at about 40° C. then the whole is left for 16 hours at ambient temperature. The reaction medium is poured into a mixture of 300 ml of saturated sodium bicarbonate solution +10 ml of triethylamine and extraction is carried out 4 times with methylene chloride. The organic phase is washed with salt water and dried. After purification by passage through silica, eluting with cyclohexane-ethyl acetate: 8-2 with 0.5% of triethylamine, 17 g of expected product (pale yellow syrup) is obtained.

ANALYSES:

| IR CHCl$_3$ (cm$^{-1}$) | |
|---|---|
| Absence OH | |
| O=C | 1736 |

STAGE 2: 2-amino-3-((tetrahydro-2H-pyran-2-yl) oxy)-2-(((tetrahydro-2H-pyran-2-yl)-oxy)-methyl)-propanenitrile.

5.6 g of the product obtained in Stage 1 above is introduced into 8 ml of ammonium hydroxide, the mixture is taken to about −5° C. and 1.58 g of ammonium chloride and 1.23 g of sodium cyanide are added successively and the reaction medium is left to rise to ambient temperature for about 40 minutes then heated at 40° C.±5° C. under agitation overnight. It is returned to ambient temperature and extraction is carried out 3 times with chloroform, the organic phase is washed with salt water and dried. After purification on silica, eluting with cyclohexane-ethyl acetate: 3-7 with 0.5% of triethylamine, 4.41 g of expected product (pale yellow syrup) is obtained.
ANALYSES:

| IR CHCl$_3$ (cm$^{-1}$) | |
|---|---|
| —CN | 2235 |
| NH$_2$ | 3390–3317 |

STAGE 3: 4-(5-imino-2-oxo-4,4-bis(((tetrahydro-2H-pyran-2-yl)-oxy)-methyl)-1-imidazolidinyl)-2-(trifluoromethyl)-benzonitrile 570 mg of the product obtained in Stage 2 above is introduced into 5 ml of isopropyl ether and 0.28 ml of triethylamine and the mixture is taken to −30° C. then a solution of 12.6 ml of 1,2-dichloroethane containing 2.32 g of the product obtained in Preparation 1 is added over one hour. 4 ml of methylene chloride is added then the reaction medium is allowed to rise to ambient temperature, left for about 2 hours and dried. After purification on silica, eluting with methylene chloride-acetone: 9-1, 700 mg of expected product is obtained.
ANALYSES:

| IR CHCl$_3$ (cm$^{-1}$) | |
|---|---|
| NH | 3442–3317 |
| —CN | 2235 |
| C=O | 1757 |
| C=N | 1670 |
| Aromatic | 1614–1575–1505 |

STAGE 4: 4-(4,4-bis(hydroxymethyl)-2,5-dioxo-1-imidazolidinyl)-2-(trifluoromethyl)-benzonitrile 300 mg of the product obtained in Stage 3 above is introduced into 3 ml of methanol and 1.5 ml of 2N hydrochloric acid and the whole is taken to reflux for one hour 30 minutes. It is returned to ambient temperature, poured into 5 ml of bicarbonate, extraction is carried out 4 times with ethyl acetate then the extracts are washed with a saturated sodium chloride solution and dried. 5 ml of methanol is added and purification is carried out on silica eluting with methylene chloride-methanol: 9-1. The residue is taken up in 20 ml of isopropanol under reflux then concentration is carried out and 225 mg of expected product (white crystals) is obtained. M.p.=207–208° C.

| IR NUJOL (cm$^{-1}$) | |
|---|---|
| OH/NH | 3525–3365–3250 |
| CN | 2240 |
| C=O | 1778–1738 |
| Aromatic | 1618–1578–1506 |

STAGE 5: 4-[4,4-bis[[(tetrahydro-2H-pyran-2-yl)oxy]methyl]-2,5-dioxo-1-imidazolidinyl]-2-(trifluoromethyl)-benzonitrile 331 mg of the product obtained in Stage 4 above, 4 ml of tetrahydrofuran, 1 ml of 3,4-dihydro-2H-pyran and 16 mg of p. toluene sulphonic acid, and H$_2$O are introduced. After 35 minutes, the reaction medium is poured into 10 ml of sodium bicarbonate+1 ml of triethylamine and extraction is carried out with 3×10 ml of chloroform, the extracts are washed with a saturated aqueous solution of sodium chloride, dried and evaporated to dryness. After chromatography on silica, eluting with methylene chloride-acetone: 9-1, 500 mg of expected product (friable white foam) is obtained.
ANALYSES:

| IR (CHCl$_3$) cm$^{-1}$ | |
|---|---|
| Absence OH, | |
| =C—NH | 3440 |
| C≡N | 2236 |
| >C=O | 1791–1736 |
| Aromatics | 1615–1576–1505 |

STAGE 6: 4-(3-(2-fluoroethyl)-4,4-bis(hydroxymethyl)-2,5-dioxo-1-imidazolidinyl)-2-(trifluoromethyl)-benzonitrile A) Condensation of 2-bromo-1-fluoroethane 530 mg of 50% sodium hydride is introduced and 5 g of the product obtained in Stage 5 above and 30 ml of dimethylsulphoxide dried over siliporite are added dropwise over about 40 minutes, and rinsing is carried out with 2 ml of dimethylsulphoxide. 20 minutes after the release of hydrogen has stopped, 1.1 ml of 2-bromo-1-fluoroethane is added in one lot. After reacting for 2 hours 30 minutes, the medium is poured into 250 ml of water containing 1 g of monopotassium phosphate, extraction is carried out 4 times with ether, the organic phase is washed with water then with salt water, dried and evaporated to dryness. Purification is carried out on silica, eluting with methylene chloride-acetone: 92.5-7.5 and in this way 5.31 g of expected product (white friable foam) is obtained.
ANALYSES:

| IR (CHCl$_3$) cm$^{-1}$ | |
|---|---|
| Absence OH and NH | |
| C≡N | 2238 |
| >C=O | 1783–1728 |
| Aromatics | 1616–1575–1505 | b) Hydrolysis of the tetrahydropyranic ethers 550 mg of the product obtained above in a) is taken up in 6 ml of methanol and 2 ml of hydrochloric acid (2N) and the solution obtained is taken to 40° C. for 40 minutes. It is then poured into 15 ml of a saturated solution of sodium bicarbonate, extraction is carried out 4 times with ethyl acetate, the extracts are dried and evaporated to dryness. Purification on silica is carried out eluting with methylene chloride-acetone: 8-2 and in this way 351 mg of expected product (white crystals) is obtained. M.p.=138–139° C.

ANALYSES:

| M.A. | % calculated | found |
|---|---|---|
| C | 48.09 | 48.1 |
| H | 3.49 | 3.5 |
| F | 20.25 | 19.9 |
| N | 11.20 | 11.5 |

| I.R. Nujol (cm$^{-1}$) | |
|---|---|
| OH/NH | 3580–3505 |
| C≡N | 2245 |

-continued

| | |
|---|---|
| >=O | 1778–1716 |
| Aromatics | 1616–1580–1512 |

STAGE 7: 4-(4,4-bis(fluoromethyl)-2,5-dioxo-3-(2-fluoroethyl)-1-imidazolidinyl)-2-(trifluoromethyl)-benzonitrile 1 ml of tetrahydrofuran is introduced, cooled down to −50° C. and 0.66 ml of diethylamino trifluorosulphide is added dropwise over about one minute, then 375 mg of the product obtained in Stage 6 above and 4 ml of tetrahydrofuran are added over 5 minutes at this temperature. The reaction medium is rinsed with 0.5 ml of tetrahydrofuran and taken to about 30° C. After one hour, it is poured slowly into 50 ml of a saturated solution of sodium bicarbonate+10 g of ice, extraction is carried out 3 times with chloroform, the organic phase is washed with salt water, dried and evaporated to dryness. Purification is carried out on silica eluting with methylene chloride-cyclohexane: 9-1 and in this way 337 mg of expected product (white crystals) is obtained. M.p.=136–137° C. ps ANALYSES:

| M.A. | % calculated | found |
|---|---|---|
| C | 47.50 | 47.5 |
| H | 2.92 | 2.8 |
| F | 30.06 | 29.9 |
| N | 11.08 | 11.0 |
| IR (CHCl$_3$) (cm$^{-1}$) | | |
| C≡N | 2295 | |
| >=O | 1787–1736 | |
| Aromatics | 1617–1577–1505 | |

EXAMPLE 2

5,5-bis(fluoromethyl)-3-(4-cyano-3-(trifluoromethyl) phenyl)-2,4-dioxo-1-imidazolidineacetonitrile STAGE 1: 5,5-bis[[(tetrahydro-2H-pyran-2-yl)oxy]methyl]-3-[4-cyano-3-(trifluoromethyl) phenyl]-2,4-dioxo-1-imidazoleacetonitrile 0.504 g of sodium hydride at 50% in oil and 5 g of the product obtained in Stage 5 of Example 1 are introduced into 40 ml of dimethylformamide on siliporite, the mixture is rinsed with dimethylformamide and after 20 minutes 0.8 ml of bromoacetonitrile in 1 ml of anhydrous dimethylformamide is added. After agitation for 50 minutes, the reaction medium is poured over 2 g of monosodium phosphate and 120 ml of water+ice, extraction is carried out with ether, the extracts are washed with a saturated solution of sodium chloride and dried. After purification on silica eluting with methylene chloride-acetone: 96-4, approx. 5 g of expected product (foam) is obtained.

ANALYSES:

| IR (CHCl$_3$) cm$^{-1}$ | |
|---|---|
| Absence of | O=C—NH |
| C≡N | 2238 |
| >C=O | 1790–1735 |
| Aromatics | 1615–1576–1505 |

STAGE 2: 5,5-bis(hydroxymethyl)-3-(4-cyano-3-(trifluoromethyl) phenyl)-2,4-dioxo-1-imidazolidineacetonitrile 4.68 g of the product obtained in Stage 1 above in solution in 50 ml of methanol and 8.8 ml of hydrochloric acid are introduced and the whole is taken to reflux for 30 minutes. 60 ml of ice-cooled water is added, extraction is carried out with ether, the ethereal phase is washed with a saturated solution of sodium chloride and dried. After purification on silica, eluting with methylene chloride-acetone: 85-15 then 8-2, the crystals obtained are taken up in 10 ml of methylene chloride, separated out and dried. In this way 2.26 g of expected product (white crystals) is obtained. M.p.=157–158° C.

ANALYSES:

| M.A. | % calculated | found |
|---|---|---|
| C | 48.92 | 49.0 |
| H | 3.01 | 2.8 |
| F | 15.48 | 15.6 |
| N | 15.21 | 15.2 |
| I.R. Nujol (cm$^{-1}$) | | |
| Absorption OH/NH | 3582–3455 | |
| C≡N | 2240 | |
| >C=O | 1782–1726 | |
| Aromatics | 1610–1574–1504 | |

STAGE 3: 5,5-bis(fluoromethyl)-3-(4-cyano-3-(trifluoromethyl) phenyl)-2,4-dioxo-1-imidazolidineacetonitrile 1 ml of tetrahydrofuran is introduced, cooled down to −50° C. and 0.66 ml of DAST then 0.368 g of the product obtained in Stage 2 above in solution in 5 ml of anhydrous tetrahydrofuran are added and rinsing is carried out with 0.5 ml of tetrahydrofuran. The reaction medium is allowed to return to ambient temperature then maintained for 30 minutes at 30° C. It is poured slowly into 30 ml of sodium hydrogen carbonate, followed by ice-cooling, extraction is carried out with ether, the extracts are washed with a saturated solution of sodium chloride and dried. After purification on silica, eluting with methylene chloride, 0.321 g of expected product (white crystals) is obtained. M.p.=125° C.

ANALYSES:

| M.A. | % calculated | found |
|---|---|---|
| C | 48.40 | 48.3 |
| H | 2.44 | 2.3 |
| F | 25.52 | 25.2 |
| N | 15.05 | 15.1 |
| I.R. Nujol (cm$^{-1}$) | | |
| C≡N | 2238 | |
| >C=O | 1788–1736 | |
| Aromatics | 1616–1578–1508 | |

EXAMPLE 3

4-(2,5-dioxo-4,4-bis(fluoromethyl)-3-ethyl-1-imidazolidinyl)-2-(trifluoromethyl)-benzonitrile STAGE 1: 4-(4,4-bis(hydroxymethyl)-2,5-dioxo-3-ethyl-1-imida-zolidinyl)-2-(trifluoromethyl)-benzonitrile The operation is carried out as in a) and b) of Stage 6 of Example 1 starting with 110 mg of 50% sodium hydride, 1 g of the product obtained in Stage 5 of Example 1, 5 ml of dimethylformamide and 0.24 ml of ethyl iodide. In this way 1.1 g of product is obtained which is taken up in 0.2 ml of methanol and 4 ml of hydrochloric acid (2N). In this way 608 mg of expected product (white crystals) is obtained.

M.p.=155–156° C.

ANALYSES:

| M.A. | % calculated | found |
|---|---|---|
| C | 50.42 | 50.5 |
| H | 3.95 | 3.9 |
| F | 15.95 | 15.6 |
| N | 11.76 | 11.6 |
| I.R. Nujol (cm$^{-1}$) | | |
| Absorption OH/NH approx. | 3330 | |
| C≡N | 2238 | |
| C=O | 1784–1722 | |
| Aromatics | 1620–1580–1510 | |

STAGE 2: 4-(2,5-dioxo-4,4-bis(fluoromethyl)-3-ethyl-1-imidazolidinyl)-2-(trifluoromethyl)-benzonitrile The operation is carried out as in Stage 7 of Example 1, starting with 1 ml of tetrahydrofuran, 0.66 ml of diethylaminotrifluorosulphide and 349 mg of the product obtained in Stage 1 above in 4 ml of tetrahydrofuran. In this way 319 mg of expected product (white crystals) is obtained. M.p.= 129–130° C.

ANALYSES:

| M.A. | % calculated | found |
|---|---|---|
| C | 49.89 | 50.0 |
| H | 3.35 | 3.2 |
| F | 26.29 | 25.95 |
| N | 11.63 | 11.6 |
| I.R. CHCl$_3$ (cm 1) | | |
| C≡N | 2238 | |
| >=O | 1787–1734 | |
| Aromatics | 1615–1578–1505 | |

EXAMPLE 4

4-(4,4-bis(fluoromethyl) 2,5-dioxo-3-(1-methylethyl)-1-imidazolidinyl)-2-(trifluoromethyl)-benzonitrile STAGE 1: 4-(4,4-bis(hydroxymethyl)-2,5-dioxo-3-(1-methylethyl)-1-imidazolidinyl)-2-(trifluoromethyl)-benzonitrile The operation is carried out as in a) and b) of Stage 6 of Example 1 starting with 110 mg of 50% sodium hydride, 1 g of the product obtained in Stage 5 of Example 1, 5.5 ml of dimethylsulphoxide and 0.3 ml of isopropyl iodide. 1.1 g of product is obtained which is taken up in 12 ml of methanol and 4 ml of 2N hydrochloric acid. In this way 574 mg of expected product (white crystals) is obtained. M.p.= 172–173° C.

ANALYSES:

| M.A. | % calculated | found |
|---|---|---|
| C | 51.75 | 51.9 |
| H | 4.34 | 4.1 |
| F | 15.35 | 15.2 |
| N | 11.32 | 11.2 |
| I.R. nujol (cm$^{-1}$) | | |
| OH/NH | 3390 | |
| C≡N | 2240 | |
| >=O | 1782–1720 | |
| Aromatics | 1618–1575–1508 | |

STAGE 2: 4-(4,4-bis(fluoromethyl)-2,5-dioxo-3-(1-methylethyl)-1-imidazolidinyl)-2-(trifluoromethyl)-benzonitrile The operation is carried out as in Stage 7 of Example 1, starting with 1 ml of tetrahydrofuran, 0.66 ml of diethylaminotrifluorosulphide and 316 mg of the product obtained in Stage 1 above in 4 ml of tetrahydrofuran. In this way 298 mg of expected product (white crystals) is obtained. M.p.= 153–154° C.

ANALYSES:

| M.A. | % calculated | found |
|---|---|---|
| C | 51.21 | 51.1 |
| H | 3.76 | 3.6 |
| F | 25.01 | 24.9 |
| N | 11.20 | 11.3 |
| I.R. CHCl$_3$ (cm$^{-1}$) | | |
| C≡N | 2238 | |
| C=O | 1787–1734 | |
| Aromatics | 1616–1578–1505 | |

EXAMPLE 5

4-(4,4-bis(fluoromethyl)-2,5-dioxo-3-(2-propynyl)-1-imidazolidinyl)-2-(trifluoromethyl)-benzonitrile STAGE 1: 4-(4,4-bis(hydroxymethyl)-2,5-dioxo-3-(2-propynyl) 1-imidazolidinyl)-2-(trifluoromethyl)-benzonitrile The operation is carried out as in a) and b) of Stage 6 of Example 1 starting with 420 mg of 50% sodium hydride, 3.86 g of the product obtained in Stage 5 of Example 1, 15 ml of dimethylformamide and 1.30 g of propargyl bromide, in 2 ml of dimethylformamide. 3.872 g of product is obtained which is taken up in 18 ml of methanol and 6 ml of 2N hydrochloric acid. In this way 993 mg of expected product (white crystals) is obtained. M.p.=125–126° C.

ANALYSES:

| M.A. | % calculated | found |
|---|---|---|
| C | 52.32 | 52.4 |
| H | 3.29 | 3.2 |
| F | 15.52 | 15.5 |
| N | 11.44 | 11.4 |

-continued

| I.R. nujol (cm$^{-1}$) | |
|---|---|
| OH/NH | 3495–3360 |
| C≡CH | 3308 |
| C≡N | 2236 |
| C=O | 1784–1730 |
| Aromatics | 1666–1576–1506 |

STAGE 2: 4-[4,4-bis[[[(trifluoromethyl)sulphonyl]oxy] methyl] 2,5-dioxo-3-(2-propynyl)-1-imidazolidinyl]-2-(trifluoromethyl)-benzonitrile 500 mg of product obtained in Stage 1 above, 8 ml of methylene chloride, 1.2 ml of pyridine and 61 mg of 4-dimethylaminopyridine are introduced, the whole is taken to about –10° C., 1 ml of triflic anhydride is added and the reaction medium is left to react at 0° C. for about 45 minutes. It is then poured into 20 ml of sodium bicarbonate, extraction is carried out 3 times with ethyl acetate, the extracts are washed with salt water and dried. In this way 982 mg of expected product (inert friable foam) is obtained.

STAGE 3: 4-(4,4-bis(fluoromethyl) 2,5-dioxo-3-(2-propynyl) 1-imidazolidinyl)-2-(trifluoromethyl)-benzonitrile 982 mg of the crude product obtained in Stage 2 above and 8 ml of tetrahydrofuran are introduced and a 1.1 M solution in tetrahydrofuran of 3 ml of tetrabutylammonium fluoride is added over about 5 minutes. After 30 minutes, the reaction medium is poured into 25 ml of 50% sodium bicarbonate, extraction is carried out 3 times with methylene chloride, the extracts are washed with water and dried. A first purification is carried out on silica eluting with methylene chloride-acetone: 99-1, then a second purification is carried out on silica eluting with cyclohexane-ethyl acetate: 7-3. In this way, after evaporation of the fractions and trituration in ether, 252 mg of expected product (white crystals) is obtained. M.p.=126–127° C.

ANALYSES:

| M.A. | % calculated | found |
|---|---|---|
| C | 51.76 | 52.0 |
| H | 2.71 | 2.7 |
| F | 25.58 | 25.3 |
| N | 11.32 | 11.1 |

| I.R. CHCl$_3$ (cm$^{-1}$) | |
|---|---|
| ≡CH | 3307 |
| C≡N | 2238 |
| C=O | 1792–1738 |
| Aromatics | 1615–1575–1505 |

EXAMPLE 6

4-(4,4-bis(fluoromethyl)-2,5-dioxo-3-(4-hydroxy-2-butyn-1-yl)-1-imidazolidinyl)-2-(trifluoromethyl)-benzonitrile STAGE 1: 4-[3-[4-(acetyloxy)-2-butyn-1-yl]-4,4-bis[[(tetrahydro-2H-pyran-2-yl)oxy]methyl]-2,5-dioxo-1-imidazolidinyl]-2-(trifluoromethyl)-benzonitrile 416 mg of 50% sodium hydride and dropwise 4 g of the product obtained in Stage 5 of Example 1 and 15 ml of dimethylformamide are introduced and the resultant mixture is rinsed with 1 ml of dimethylformamide. 10 minutes after the end of the release of hydrogen, 3.2 g of 4-bromo-2-butyne-1-ol acetate prepared as described in J. W. Lown GENE 149, 81 (1994) and 2 ml of dimethylformamide are added, and rinsing is carried out with 0.5 ml of dimethylformamide. After one hour 30 minutes, the reaction medium is poured into 100 ml of water containing 0.5 g of monopotassium phosphate, extraction is carried out 4 times with ether, the organic phase is washed with water and with salt water and dried. Purification is carried out by chromatography on silica eluting with methylene chloride-acetone: 95-5 and 4.47 g of expected product (orange resin) is obtained.

ANALYSES:

| I.R. CHCl$_3$ (cm$^{-1}$) | |
|---|---|
| C≡N | 2236 |
| > = O | 1735–1729 |
| Aromatics | 1616–1575–1505 |

STAGE 2: 4-[3-[4-(acetoxy)-2-butyn-1-yl]-4,4-bis[[(hydroxymethyl]-2,5-dioxo-1-imidazolidinyl]-2-(trifluoromethyl)-benzonitrile 4.4 g of the product obtained in Stage 1 above, 14 ml of tetrahydrofuran, 28 ml of acetic acid and 7 ml of water are introduced and the whole is heated to 60° C.±5° C. for 4 hours. The acetic acid is evaporated off, 100 ml of ethyl acetate is added, followed by washing with bicarbonate and drying. After chromatography on silica eluting with methylene chloride-acetone: 85-15, 1.99 g of expected product (white foam) is obtained.

ANALYSES:

| I.R. CHCl$_3$ (cm$^{-1}$) | |
|---|---|
| OH | 3618–3548 |
| C≡N | 2235 |
| > = O | 1784–1729 |
| Aromatics | 1617–1607–1572–1505 |

STAGE 3: 4-[3-[4-(acetoxy)-2-butyn-1-yl]-4,4-bis(fluoromethyl)-2,5-dioxo-1-imidazolidinyl]-2-(trifluoromethyl)-benzonitrile The operation is carried out as in Stages 2 and 3 of Example 5, starting with 439 mg of the product obtained in Stage 2 above, 6 ml of methylene chloride, 1.35 ml of 2,6-lutidine, 50 mg of 4-dimethylaminopyridine and 1 ml of trifluoromethane sulphonic anhydride is added at a temperature of 0 to 5° C. The reaction medium is left to react for one hour at this temperature then poured into a mixture of 50 ml of sodium bicarbonate-ethyl acetate: 1—1, followed by decanting, washing with salt water and drying. Then the product is taken up in 6 ml of tetrahydrofuran, and a 1.1 M solution of 2.3 ml of tetrabutylammonium fluoride in tetrahydrofuran is added. The medium is poured into 60 ml of sodium bicarbonate-ethyl acetate: 1—1, followed by decanting, washing with salt water and drying. After purification by chromatography on silica eluting with methylene chloride-ethyl acetate: 95-5, 177 mg of expected product (resin) is obtained.

ANALYSES:

| I.R. CHCl$_3$ (cm$^{-1}$) | |
|---|---|
| C≡N | 2238 |
| > = O | 1792–1757 |
| Aromatics | 1615–1575–1505 |

STAGE 4: 4-(4,4-bis(fluoromethyl)-2,5-dioxo-3-(4-hydroxy-2-butyn-1-yl)-1-imidazolidinyl)-2-(trifluoromethyl)-benzonitrile 1 g of the product obtained in Stage 3 above, 18 ml of methanol and 4.5 ml of 2N hydrochloric acid are introduced then left for one hour 30 minutes at 50° C. The reaction medium is then returned to ambient temperature, poured into 30 ml of sodium bicarbonate, extraction is carried out with ethyl acetate 3 times, the extracts are washed with salt water and dried. After chromatography on silica eluting with methylene chloride-acetone: 85-15, 780 mg of expected product (white crystals) is obtained. M.p.=131–132° C.
ANALYSES:

| I.R. CHCl$_3$ (cm$^{-1}$) | |
|---|---|
| OH | 3610 |
| C≡N | 2238 |
| > = O | 1792–1736 |
| Aromatics | 1615–1576–1505 |

EXAMPLE 7

4-(4,4-bis(fluoromethyl)-2,5-dioxo-3-methyl-1-imidazolidinyl)-2-(trifluoromethyl)-benzonitrile 1 ml of tetrahydrofuran is introduced, taken to −30° C., 3.24 ml of diethylaminotrifluorosulphide, then 0.12 g of the product of Example 24 of FR 2715402 are added and the whole is rinsed with 0.5 ml of tetrahydrofuran, then left to rise to ambient temperature and taken to +30° C. After 40 minutes, the reaction medium is poured over 5 g of ice in 20 ml of sodium bicarbonate, extraction is carried out 5 times with methylene chloride, the organic phase is washed with salt water and dried. Purification is carried out by chromatography on silica eluting with methylene chloride-ethyl acetate: 99-1 and in this way 111 mg of expected product (white crystals) is obtained. M.p.=137–138° C.
ANALYSES:

| M.A. | % calculated | found |
|---|---|---|
| C | 48.42 | 48.2 |
| H | 2.90 | 2.8 |
| F | 27.35 | 26.9 |
| N | 12.10 | 11.9 |

| I.R. CHCl$_3$ (cm$^{-1}$) | |
|---|---|
| C≡N | 2235 |
| > = O | 1790–1735 |
| Aromatics | 1617–1580–1505 |

EXAMPLE 8

4-(3-(4-hydroxy-2-butyn-1-yl)-4,4-dimethyl-2,5-dione-1-imidazolidinyl)-2-(trifluoromethyl)-benzonitrile a) Condensation of the 4-tertbutyldimethylsiloxy-2-butyne chain 103 mg of 50% sodium hydride is introduced, 570 mg of the product of Example 8 of EP 0494819, 3.5 ml of dimethylformamide are added and the whole is rinsed with 0.5 ml of dimethylformamide. 20 minutes after the release of hydrogen has stopped, 0.5 g of 1-bromo-4-tertbutyldimethylsiloxy-2-butyne prepared as indicated in J. W. Lown et al. GENE 149, 81 (1994) is added and the reaction medium is taken to $_{40}$° C. After 50 minutes, it is poured into 40 ml of water containing about 0.5 g of monopotassium phosphate, extraction is carried out 4 times with ether, the organic phase is washed with water then with salt water and dried. Purification is carried out by chromatography on silica eluting with methylene chloride-acetone: 98-2 and 732 mg of pale syrup is obtained.

b) Hydrolysis of the silylated ether

The 732 mg of product obtained in a) above is taken up in 7.5 ml of methanol and 1.5 ml of 2N hydrochloric acid. After 40 minutes, the reaction medium is poured into 30 ml of 50% sodium bicarbonate, extraction is carried out 3 times with ethyl acetate, the extracts are washed with salt water and dried. After purification by chromatography on silica eluting with methylene chloride-acetone: 92.5-7.5, 516 mg of expected product (white crystals) is obtained. M.p.=125–126° C.
ANALYSES:

| M.A. | % calculated | found |
|---|---|---|
| C | 55.89 | 56.0 |
| H | 3.86 | 3.8 |
| F | 15.60 | 15.9 |
| N | 11.50 | 11.7 |

| I.R. CHCl$_3$ (cm$^{-1}$) | |
|---|---|
| OH | 3608 |
| C≡N | 2230 |
| > = O | 1783–1726 |
| Aromatics | 1616–1575–1505 |

EXAMPLE 9

4-[2,4-dioxo-1-(4-hydroxybutyl)-1,3-diazaspiro-[4.5]decan-3-yl]-2-(trifluoromethyl)-benzonitrile STAGE 1: 1-amino-cyclohexanecarbonitrile 1.23 g of sodium cyanide, 1.58 g of ammonium chloride and 8 ml of ammonium hydroxide are introduced, the whole is taken to 0° C. and 2.1 g of cyclohexanone is added. The reaction medium is left to return to ambient temperature under agitation for 18 hours, diluted in a small amount of water and decanted. The aqueous phase is extracted with methylene chloride, the organic phases are combined, washed with salt water, dried, filtered and concentrated. In this way 2.38 g of expected product (colourless oil) is obtained.
ANALYSES:

| I.R. CHCl$_3$ (cm$^{-1}$) | |
|---|---|
| NH$_2$ | 3380–3315 |
| CN | 2225 |

STAGE 2: 4-[2-imino-4-oxo-1,3-diazaspiro[4.5]decan-3-yl]-2-(trifluoromethyl)-benzonitrile 3.75 ml of an 18% 1,2-dichloroethane solution of the product of Preparation 1 is introduced, 10 ml of dry dichloroethane and 0.22 ml of triethylamine are added, the whole is taken to −30° C., 558 mg of the product obtained in Stage 1 above in 2 ml of dichloroethane is added and the reaction medium is left at ambient temperature for 18 hours. After chromatography on silica eluting with methylene chloride-acetone: 8-2, 1.10 g of expected product (white solid) is obtained.

ANALYSES:

| I.R. (cm$^{-1}$) | |
| --- | --- |
| OH/NH | 3370–3290 |
| CN | 2240 |
| C=O | 1743 |
| C=N | 1678 |
| Aromatics | 1615–1606–1572–1542–1508 |

STAGE 3: 4-(2,4-dioxo-1,3-diazaspiro(4.5)decan-3-yl)-2-(trifluoromethyl)-benzonitrile 1.10 g of the product obtained in Stage 2 above, 3 ml of 6N hydrochloric acid and 8 ml of ethanol are introduced, the mixture is taken to reflux for one hour, cooled down to ambient temperature, neutralized by the addition of sodium hydrogen carbonate, extracted with ethyl acetate. The organic phases are combined, washed with water, dried, filtered and concentrated. After chromatography on silica eluting with methylene chloride-acetone: 9-1, then recrystallization from isopropanol, 470 mg of expected product (white solid) is obtained. M.p.=187° C.

ANALYSES:

| M.A. | % calculated | found |
| --- | --- | --- |
| C | 57.0 | 56.8 |
| H | 4.15 | 4.0 |
| N | 12.50 | 12.5 |
| F | 16.9 | 16.8 |

| I.R. CHCl$_3$ (cm$^{-1}$) | |
| --- | --- |
| NH | 3450 |
| CN | 2235 |
| C=O | 1787–1727 |
| Aromatics | 1617–1575–1505 |

STAGE 4: 4-[2,4-dioxo-1-(4-hydroxybutyl)- 1,3-diazaspiro-[4.5]decan-3-yl]-2-(trifluoromethyl)-benzonitrile 28 mg of 50% sodium hydride and 3 ml of dimethylformamide are introduced, agitation is carried out at ambient temperature for 5 minutes, 170 mg of the product obtained in Stage 3 above is added and the whole is left under agitation for 20 minutes until the release of hydrogen has stopped. 202 mg of O-trimethylsilyl-4-iodo-n-butanol is then added and the reaction medium is left under agitation for 2 hours. After hydrolysis using saturated ammonium chloride, extraction is carried out with ethyl acetate. The organic phases are combined, washed with water, dried, filtered and concentrated. The residue is solubilized in 10 ml of methanol and 0.5 ml of 2N hydrochloric acid is added. After agitation for 5 minutes, the solution is neutralized by the addition of saturated sodium hydrogen carbonate and extraction is carried out with ethyl acetate. The organic phases are combined, dried, filtered and concentrated. After chromatography on silica eluting with methylene chloride-acetone: 9-1, 158 mg of expected product (white solid) is obtained. M.p.=145° C.

ANALYSES:

| M.A. | % calculated | found |
| --- | --- | --- |
| C | 58.8 | 58.8 |
| H | 5.4 | 5.2 |
| F | 13.9 | 13.6 |
| N | 10.3 | 10.1 |

| I.R. CHCl$_3$ (cm$^{-1}$) | |
| --- | --- |
| OH | 3626 |
| CN | 2236 |
| C=O | 1772–1719 |
| Aromatics | 1615–1575–1505. |

EXAMPLE 10

Tablets were prepared having the following composition:

Product of Example 6 . . . 100 mg

Excipient s.q. for a tablet completed at . . . 300 mg (Detail of the excipient: lactose, starch, talc, magnesium stearate).

PHARMACOLOGICAL STUDY OF THE
PRODUCTS OF THE INVENTION

1) Study of the Affinity of the Products of the Invention for the Androgen Receptor Male Sprague Dawley EOPS rats weighing 180–200 g, castrated 24 hours previously, are sacrificed, the prostates are removed, weighed and homogenized at 0° C. using a Potter glass flask, in a buffered solution (10 mM Tris, 0.25M saccharose, 0.1 mM PMSF (phenylmethanesulphonylfluoride), 20 mM sodium molybdate, HCl pH 7.4; to which 2 mM of DTT (DL dithiothreitol) is added extemporaneously), at the rate of 1 g of tissue per 8 ml of buffer.

The homogenate is then ultracentrifuged at 0° C. for 30 minutes at 209,000 g. Aliquots of the supernatant obtained (=cytosol), are incubated for 30 minutes and 24 hours at 0° C., with a constant concentration (T) of tritiated testosterone and in the presence of increasing concentrations (0 to 2500×10$^{-9}$M), either of unlabelled testosterone, or of the products to be tested. The concentration of bound tritiated testosterone (B) is then measured in each incubate by the method of adsorption with carbon dextran.

Calculation of the Relative Bond Affinity (RBA).

The following 2 curves are drawn: the percentage of bound tritiated hormone B/T as a function of the logarithm of the concentration of unlabelled reference hormone and B/T as a function of the logarithm of the concentration of unlabelled product tested. The straight line of the equation $I_{50}$=(B/Tmax+B/Tmin)/2 is determined.

B/Tmax=% of bound tritiated hormone for an incubation of this tritiated hormone at the concentration (T).

B/Tmin=% of bound tritiated hormone for an incubation of this tritiated hormone at the concentration (T) in the presence of a large excess of unlabelled hormone (2500×10$^{-9}$M).

The intersections of the straight line $I_{50}$ and the curves allow the evaluation of the concentrations of the unlabelled reference hormone (CH) and of the tested unlabelled product (CX) which inhibit by 50% the binding of the tritiated hormone on the receptor. The relative bond affinity (RBA) of the tested product is determined by the equation RBA=100 (CH)/(CX).

The following results are obtained, expressed in RBA. Reference product (Testosterone): 100

TABLE 1

| Product of example | RBA: Incubation 24 hours |
|---|---|
| 1 | 42 |
| 3 | 43 |

2) Determination of the Reducing Effect on the Costo-vertebral Gland of the Hamster The local activity (topical) of an antiandrogen is determined by the reduction which it brings about in the surface area of the costovertebral gland of the hamster (hereafter C.V.G.), an androgen-dependent organ situated on the flanks of the animal.

The animals are male hamsters weighing about 140 g, 14 weeks old and originating from the Charles River breed (USA), they are subjected to a long photoperiod (16 hours of light, 8 hours of darkness). The animals are treated every day, except for the weekend, for 3 weeks (14 administrations). The product to be tested is applied, by topical route, on the right-hand C.V.G., the left-hand one serving as the control. The surface of the gland has been shaved beforehand. The animals are sacrificed by bleeding the carotid artery 24 hours after the last treatment. The C.V.G.'s are removed, measured and weighed. The local activity of a product is determined by the % of reduction in the surface area of the C.V.G. which it induces in comparison with the 1st day of the experiment and compared to the animals treated with solvent only.

TABLE 2

| Product of example | % CVG reduction with 3 µg/jour |
|---|---|
| 1 | −32 |
| 3 | −33 |
| 9 | −25 |

3) Determination of the Reducing Effect of the Weight of the Prostate in an Intact Male Rat The systemic activity of an antiandrogen is determined by the reduction in the weight of the prostate which it brings about in an intact animal.

The animals used are male rats of the Sprague Dawley strain weighing about 200 g, 7 weeks old, originating from the Iffa Credo breed (France). The experiment is carried out over two weeks, except for the weekend.

The product can be administered by oral, sub-cutaneous or percutaneous route.

The solvents used are then: by oral route: 0.5% aqueous solution of methylcellulose under a volume of 5 ml/kg, by sub-cutaneous route: wheatgerm oil in 10% ethanol under a volume of 0.2 ml/kg, and by percutaneous route: ethanol under a volume of 50 ul on previously-shaved skin.

The treatment is carried out from day 0 to day 4 then (after the weekend) from day 7 to day 10. The animals are sacrificed the day after the last treatment by bleeding the carotid artery, the prostates are removed and fixed in demineralized water containing 10% formol for 72 hours. They are then dissected and weighed. The blood is removed in order to determine, by radioimmunological assay, the amount of seric testosterone. The antiandrogen activity of the product is expressed as % reduction in the weight of the prostates and as % variation in the amounts of testosterone compared to the animals treated by the solvent only.

TABLE 3

| Product of example | % reduction in the prostate weight with 3 mg/kg P.O. |
|---|---|
| 1 | −27 |
| 3 | −20 |
| 8 | −35 |

What is claimed is:

1. A compound selected from the group consisting of 4-(4,4-bis(fluoromethyl)-2,5-dioxo-3-(4-hydroxy-2-butyn-1-yl)-1-imidazolidinyl)-2-(trifluoromethyl)-benzonitrile, 4-(3-(4-hydroxy-2-butyn-1-yl) -4,4-dimethyl-2,5-dioxo-1-imidazolidinyl)-2-(trifluoromethyl)-benzonitrile, 4-[2,4-dioxo-1-(4-hydroxybutyl)-1,3-diazaspiro[4,5]decan-3-yl]-2-(trifluoromethyl)-benzonitrile and the addition salts with non-toxic, pharmaceutically acids.

2. An antiandrogenic composition comprising an antiandrogenically effective amount of a compound of claim 1 and an inert pharmaceutical carrier.

3. A method of inducing antiandrogenic activity in warm-blooded animals comprising administering to warm-blooded animals an antiandrogenically effective amount of a compound of claim 1.

* * * * *